United States Patent [19]

Jain

[11] Patent Number: 5,776,478
[45] Date of Patent: Jul. 7, 1998

[54] INSECT REPELLENT

[76] Inventor: Pritam Sain Jain, 1750 Boyd Street, Regina, Saskatchewan, Canada, S4V 1S6

[21] Appl. No.: 757,324

[22] Filed: Nov. 27, 1996

[51] Int. Cl.$^6$ ............................................. A01N 25/04
[52] U.S. Cl. .......................... 424/405; 424/406; 424/407; 424/DIG. 10; 424/195.1; 514/919
[58] Field of Search ........................ 424/405–407, 424/DIG. 10, 195.1; 514/919

[56] References Cited

U.S. PATENT DOCUMENTS

| | | | |
|---|---|---|---|
| 4,853,413 | 8/1989 | Katz et al. | 514/526 |
| 5,364,626 | 11/1994 | Hasegawa et al. | 424/403 |
| 5,543,149 | 8/1996 | Rubin | 424/405 |

FOREIGN PATENT DOCUMENTS 2147595  11/1995  Canada.

OTHER PUBLICATIONS

Lesser: Insect Repellents Feb. '41:48.2 The Drug & Cosmetic Industry pp. 149, 150.

West & Todd Textbook of Biochemistry 4th Ed. 1966 pp. 828, 832.

*Primary Examiner*—Neil S. Levy
*Attorney, Agent, or Firm*—Adrian D. Battison; Murray E. Thrift

[57] ABSTRACT

Plant extracts (oils and juices) are used in compositions for repelling insects for avoiding their annoyance, bites and reactions. The compositions are safe for use on the skin of people of all age groups as well as on their clothes. It is a three in one product that repels insects, protects the skin against the adverse effects of ultraviolet light and works as a post-bite treatment as well. The solution is non-flammable and has natural scents.

2 Claims, No Drawings

INSECT REPELLENT

The present invention relates to processes and compositions for repelling insects and for treating insect bites.

BACKGROUND OF THE INVENTION

Biting insects pose a significant problem not only because of the annoyance from their bites and stings, but also because of the potential health risks due to transmission of diseases from these bites. In light of this, there is significant demand for effective insect repellents. Ideally, an insect repellent should be safe to use on all age groups and most importantly, non-toxic.

The majority of the insect repellents currently available contain a chemical n,n-diethyl-m-toluamide (DEET) as the repelling agent or active ingredient. DEET is readily absorbed through the skin and enters into the blood stream. As a result, it has been shown to adversely affect the nervous system. Specifically, DEET has caused seizures and even death in some individuals. As a consequence, several state public health departments have issued warnings about the possible hazards of overzealous application of products containing DEET. Also, the United States Military now recommends use of repellents with less than 33% DEET. In addition, the American Academy of Pediatrics recommends that repellents used on children contain no more than 10% DEET.

Insect repellents containing DEET are also not recommended for use over cuts, wounds or irritated skin, nor next to the eyes or mouth. They are also not recommended for infants and toddlers as well as on acetate, rayon, spandex, dynel and other synthetic clothes, furniture, plastic, watch crystals, leather and painted and washable surfaces including automobiles. It is therefore quite clear that a safer alternative is needed.

One alternative is citronella oil, which is known to have insect repelling properties. Currently, citronella oil is used as an insect repellent primarily in candles and adhesive patches. As an example, Canadian Patent Application 2,147,595 teaches an adhesive patch comprising 99.9% citronella oil for repelling insects and 0.1% lemongrass oil or spearmint oil to impart fragrance, thereby making the mixture non-offensive to humans. While some creams and lotions containing citronella oil are commercially available, citronella oil caused burning and/or irritation when applied to the facial area of test subjects in our experiments.

Additionally, U.S. Pat. No. 5,364,626 teaches a composition containing lemon oil for use in repelling animals such as dogs or cats. However, this patent does not envision the use of lemon oil as an insect repellent.

SUMMARY OF THE INVENTION

It is one object of the invention, therefore, to provide a method for repelling insects and a method for treating insect bites. It is a further object of the invention to provide compositions for repelling insects and treating insect bites that are safe and non-toxic. Additionally, these compositions will provide protection against the adverse effects of ultraviolet light on the skin.

According to a first aspect of the invention, there is provided a method of repelling insects comprising:

providing a mixture comprising:
  an active ingredient selected from the group consisting of lemon oil, cedarwood oil, and mixtures thereof; and
  a solvent;
and repelling insects by applying the mixture to areas desired for protection.

Preferably, the mixture includes a source of an antioxidant for stabilizing the active ingredient. The antioxidant may be provided by a mixture of ascorbic acid and citric acid, or using natural sources of these chemicals, such as lime juice or lemon juice. The ascorbic acid will stabilize the active ingredients in the natural oils by acting as an anti-oxidant while the citric acid will in turn stabilize the ascorbic acid. The end result is that the longevity of the repellent properties of the mixture is significantly increased.

The solvent may be an alcohol, such as isopropyl alcohol, commonly known as rubbing alcohol. Aside from solubilizing the active ingredients of the above oils, the alcohol will also act as a preservative and disinfectant within the mixture.

The mixture may consist essentially of:
- 5–60% active ingredient, selected from the group consisting of lemon oil, cedarwood oil and mixtures thereof;
- 15–60% source of an antioxidant or a mixture of ascorbic acid and citric acid, selected from the group consisting of lemon juice and lime juice; and
- 0–95% isopropyl alcohol;
- 0–95% water;
- <1% oil emulsifier when the mixture is a water-base (no alcohol); and
- <1% antioxidant when the mixture does not contain organic acids.

The main reason for the wide range of concentrations in the active ingredient in the above mixtures is to provide flexibility for varying the compositions according to their intended use. For example, a mixture designed for extended protection from insects would contain a greater proportion of active ingredient than a mixture designed for shorter periods of protection. Also, a mixture for repelling insects designed to be applied on solid structures such as wood or clothing would contain a much higher concentration of active ingredient.

The wide range of possible concentrations of the remaining components of the above-described mixture provides flexibility when preparing mixtures to meet the needs of all types of consumers. In some mixtures, the active ingredients may be dissolved in alcohol only while others may be completely water-base (no alcohol), therefore requiring a small amount of suitable oil emulsifier (less than 1%). Also, some mixtures may not contain any organic acids, due to the sensitivity of the skin of some individuals to acidic compounds. In such mixtures, a suitable anti-oxidant (less than 1%), such as Vitamin E, will be added in place of ascorbic and citric acid to maintain stability of the active ingredients. A mixture of this type will repel insects but may not provide a post-bite treatment.

Preferably, the mixture may consist essentially of:
- 25% active ingredient, selected from the group consisting of lemon oil, cedarwood oil and mixtures thereof;
- 25% isopropyl alcohol;
- 40% a mixture of ascorbic acid and citric acid, selected from the group consisting of lemon juice and lime juice; and
- 10% water.

According to a second aspect of the invention, there is provided a method of repelling insects comprising:

providing a mixture comprising:
  an active ingredient selected from the group consisting of lemon oil, cedarwood oil and mixtures thereof;

an oil emulsifier; and
water; and
repelling insects by applying the mixture to areas desired for protection.

Of note is that the above-described mixture does not contain any alcohol. Rather, it contains a suitable oil emulsifier to emulsify the active ingredients of the natural oils in water. This mixture is designed for consumers who would prefer not to use alcohol-based solutions.

The mixture may include a source of an antioxidant for stabilizing the active ingredients The antioxidant may be a mixture of ascorbic acid and citric acid selected from the group consisting of lemon juice and lime juice.

According to a third aspect of the invention, there is provided a method of treating pain and swelling caused by an insect bite comprising:

providing a solution comprising:
an active ingredient selected from the group consisting of one or more of the following: non-toxic organic acids; lemon juice; lime juice; ascorbic acid and citric acid;
locating the insect bite in an afflicted region; and
applying said mixture topologically and rubbing over the afflicted region,
thereby reducing the pain and swelling by neutralizing alkaline agents within the insect bite. Examples of non-toxic organic acids include ascorbic acid, citric acid and acetic acid, although this list is by no means exhaustive or complete. Once this mixture is applied to the skin, it will also lessen the severity of any subsequent insect bites.

The solution may include a preservative.

Preferably, the mixture includes a scenting agent selected from the group consisting of lemon oil, cedarwood oil and mixtures thereof. Aside from making the mixture more aesthetically pleasing, these scents will also act to prevent further bites as they contain active ingredients that will act to repel insects.

The solvent may be an alcohol, such as isopropyl alcohol. Besides solubilizing the scenting and insect repelling agents, the alcohol will also act as a preservative and disinfectant within the mixture.

The mixture may consist essentially of:
15–60% active ingredient, selected from the group consisting of non-toxic organic acids, lemon juice, lime juice, ascorbic acid and citric acid;
5–60% scenting agent, selected from the group consisting of lemon oil, cedarwood oil and mixtures thereof;
0–95% isopropyl alcohol;
0–95% water; and
<1% oil emulsifier when the mixture is water-base (no alcohol).

The composition of the mixture may be varied according to preference and intended use. For example, a mixture designed for quick relief of swelling and pain would contain a greater proportion of active ingredient than a mixture designed for slow relief. Additionally, varying the relative concentrations of the natural oils and the source and amount of ascorbic acid and citric acid will alter the scent of the mixture.

Preferably, the mixture may consist essentially of:
40% active ingredient, selected from the group consisting of non-toxic organic acids, lemon juice, lime juice, ascorbic acid and citric acid;
25% isopropyl alcohol;
25% scenting agent, selected from the group consisting of lemon oil, cedarwood oil and mixtures thereof; and
10% water.

According to a fourth aspect of the invention, there is provided a composition comprising:
an active ingredient selected from the group consisting of lemon oil, cedarwood oil and mixtures thereof;
a source of ascorbic acid and citric acid; and
a solvent.

Preferably, the source of citric acid and ascorbic acid is selected from the group consisting of lemon juice and lime juice.

The solvent may be an alcohol, such as isopropyl alcohol. Besides solubilizing the active ingredients of the natural oils, the alcohol will also act as a preservative and disinfectant within the composition.

The composition may consist essentially of:
5–60% active ingredient selected from the group consisting of lemon oil, cedarwood oil and mixtures thereof;
15–60% source of citric acid and ascorbic acid, selected from the group consisting of lemon juice and lime juice;
0–95% isopropyl alcohol;
0–95% water; and
<1% oil emulsifier when the mixture is a water-base (no alcohol).

Preferably, the composition may consist essentially of:
25% active ingredient selected from the group consisting of lemon oil, cedarwood oil and mixtures thereof;
25% isopropyl alcohol;
40% source of ascorbic acid and citric acid, selected from the group consisting of lemon juice and lime juice; and
10% water.

The above-described composition has several useful properties. For example, the natural oils contain active ingredients that will act to repel insects. The natural juices provide ascorbic acid and citric acid which will stabilize the active ingredients of the natural oils as described above. Furthermore, the ascorbic acid and citric acid act as an effective post-bite treatment. This is based on the fact that it is the alkaline solution injected by the insect that produces the reaction of pain and swelling. However, the organic acids present in the natural fruit juices will neutralize the alkaline solution, thereby reducing their effect. Natural sources of ascorbic acid and citric acid are used rather than the individual components because fruit juices contain both forms of ascorbic acid: L-ascorbic acid and dehydro-L-ascorbic acid. These two forms of ascorbic acid act as a redox couple, meaning that they act in concert as an anti-oxidant. One of the roles of anti-oxidants within the cell is to hydroxylate potential oxidants such as superoxide and hydroxyl radicals. This prevents the oxidants from damaging the cell membrane by peroxidizing the lipids. Considering that one of the effects of exposure to ultraviolet rays is the generation of superoxide and hydroxyl radicals, the presence of both forms of ascorbic acid in the above-described composition will lessen the damage caused by ultraviolet rays. Given that insect repellents are generally used outdoors, the anti-ultraviolet activity of the above-described composition is a significant benefit.

An obvious advantage of the present invention is that the mixtures herein described contain natural components that are known to be non-toxic. Lemon oil and cedarwood oil have long been used as scenting agents and have not caused any adverse reactions in the trials described below, even when applied to sensitive areas of the skin, such as around the eyes. Furthermore, the natural juices contain ascorbic acid and citric acid. Aside from providing the benefits described above, these organic acids are also readily biodegraded: citric acid is an intermediate in the Krebs Cycle; ascorbic acid is more commonly known as Vitamin C and has been ascribed several activities aside from being an anti-oxidant, such as involvement in wound healing and enhanced immune response. Thus, there are likely to be additional health benefits aside from repelling insects and treating insect bites derived from using this composition.

Plant extracts (oils and juices) are used in compositions for repelling insects for avoiding their annoyance, bites and reactions. The compositions are safe for use on the skin of people of all age groups as well as on their clothes. It is a three in one product that repels insects, protects the skin against the adverse effects of ultraviolet light and works as a post-bite treatment as well. The solution is non-flammable and has natural scents.

BRIEF DESCRIPTION OF THE TABLES

Table 1—Results of a study on the effectiveness of an insect repellent prepared according to Formula Example 3 and lemon juice as a post-bite treatment solution at the Mosquito Laboratory in Winnipeg, Manitoba, Canada on Jun. 26, 1996.

Table 2—Results of a study on the effectiveness of insect repellents prepared according to Formula Examples 1 and 2 and lemon juice as a post-bite treatment solution at the Mosquito Laboratory in Winnipeg, Manitoba, Canada on Jun. 26, 1996.

Table 3—Results of a study on the effectiveness of an insect repellent prepared according to Formula Example 1 and lemon juice as a post-bite treatment solution at New Delhi, India on Aug. 5, 1994.

Table 4—Results of a study on the effectiveness of an insect repellent prepared according to Formula Example 2 and lemon juice as a post-bite treatment solution at Panipat, Haryana, India on Aug. 12, 1994.

Table 5—Results of a study on the effectiveness of an insect repellent prepared according to Formula Example 3 and lemon juice as a post-bite treatment solution at Hissar, Haryana, India on Aug. 19, 1994.

Table 6—Results of a study on the effectiveness of an insect repellent prepared according to Formula Example 1 and lemon juice as a post-bite treatment solution in backyard and vegetable garden areas in Regina, Saskatchewan, Canada on Jul. 14, 1995.

Table 7—Results of a study on the effectiveness of insect repellents prepared according to Formula Examples 1, 2 and 3 and lemon juice as a post-bite treatment solution in bush areas of Regina, Saskatchewan, Canada on Jun. 16, 1996.

DETAILED DESCRIPTION

The present invention is described in detail based on examples; however, the invention is not limited to the examples.

Formula Example 1:
  25 parts lemon oil
  25 parts isopropyl alcohol
  40 parts lemon juice
  10 parts water
Formula Example 2:
  25 parts cedarwood oil
  25 parts isopropyl alcohol
  40 parts lemon juice
  10 parts water
Formula Example 3:
  10 parts cedarwood oil and 15 parts lemon oil, such that a total of 25 parts natural oil added
  25 parts isopropyl alcohol
  40 parts lemon juice
  10 parts water Varying the relative amounts of lemon oil and cedarwood oil alters the scent of the mixture, but does not alter the effectiveness of the mixture as an insect repellent, as described below.

In all three examples, the compositions are prepared as follows: the total volume of natural oils are added to the isopropyl alcohol and the solution is mixed by shaking for fifteen seconds. Next, the lemon juice and the water are added and the composition is mixed by shaking for an additional fifteen seconds.

The functions of the ingredients are as follows. The natural oils (lemon oil, cedarwood oil and mixtures thereof) provide the active ingredient for repelling the insects. The isopropyl alcohol acts as a solvent of the active ingredients of the natural oils and also acts as a preservative and disinfectant within the mixture. Clearly, alcohols other than isopropyl alcohol may be used for this purpose. The lemon juice provides ascorbic acid and citric acid, which act to stabilize the active ingredients of the natural oils. These organic acids will also act to neutralize the alkaline solution injected during an insect bite, thereby reducing pain and swelling. Furthermore, lemon juice contains both forms of ascorbic acid, also known as Vitamin C. As a consequence, this mixture will also provide the benefits associated with Vitamin C, including anti-oxidant activity. This in turn means that the mixture will reduce some of the harmful effects of ultraviolet rays by scavenging the superoxide and hydroxyl radicals generated by exposure to ultraviolet light. Although lemon juice is used in the example, any natural juice containing high levels of ascorbic acid and citric acid, such as lime juice, may be used. The water acts as a solvent, diluant and filler. Ideally, any water source may be used, such as distilled water, deionized water or mineral water.

Several laboratory and field experiments involving individuals from a variety of age groups were performed. These experiments were carried out at various times of day and at several different locations, such as backyard areas, garden areas and bush areas, in order to determine the effectiveness of the compositions of the Formula Examples as insect repellents under the greatest possible variety of conditions. The results of a sampling of the experiments are shown in Tables 1–7, and five of these experiments are discussed below.

Trial Example 1

The results of Trial Example 1 are summarized in Table 1. The source of insects were mosquitoes bred in a Plexiglas box to a high density under laboratory conditions. Initially, the untreated left hand of Subject #1 was placed in the Plexiglas box containing the mosquitoes as a control and to check the biting nature of the mosquitoes. During a ten second exposure, six mosquitoes landed on the untreated left hand and four mosquito bites were incurred. At this point, Subject #1 removed his left hand from the Plexiglas box and lemon juice was applied to the areas with mosquito bites. To maintain the integrity of the experiment, lemon juice was used rather than the above-described compositions. However, the lemon juice does not lose any effectiveness at treating insect bites when part of the compositions of the Formula Examples. Following application, the pain and swelling from the insect bites on the left hand ceased. Next, the composition according to Formula Example 3 was applied to the right hand of Subject #1 and this hand was placed in the Plexiglas box containing the mosquitoes. During a two minute exposure, no insect bites occurred and no mosquitoes landed on the treated right hand. An interval of one hour and forty-five minutes passed before the right hand of the subject was placed in the Plexiglas box again. Despite the time elapsed since application, no further treatments during this interval, no mosquito bites occurred during a further two minute exposure.

Trial Example 2

The results of Trial Example 2 are summarized in Table 2. The untreated left hand of Subject #2 was placed in a Plexiglas box containing mosquitoes grown under laboratory conditions as described above. During a ten second exposure, seven mosquitoes landed on the untreated hand and four mosquito bites occurred. Lemon juice was applied to the mosquito bites and the pain and swelling ceased immediately. To maintain the integrity of the experiment, lemon juice was used rather than the above-described compositions. However, the lemon juice does not lose any effectiveness at treating insect bites when part of the compositions of the Formula Examples. The composition of Formula Example 1 was applied to the right hand of Subject #2 while the composition of Formula Example 2 was applied to the left hand of Subject #1. When the left hand of Subject #1 was placed in the Plexiglas box for a period of two minutes, no further bites occurred. An interval of ninety minutes passed, and the left hand of Subject #1 was again placed in the Plexiglas box for an additional two minutes. As before, no insect bites occurred. The same process was repeated using the right hand of Subject #2. In this instance, no mosquito bites were incurred, either during the initial two minute exposure or during the second two minute exposure following a ninety minute interval.

The results of the above experiments clearly indicate that the compositions of the Formula Examples act as effective insect repellents in a controlled setting. Specifically, no bites occurred on the treated hands during a two minute exposure while multiple bites occurred on an untreated hand during only a ten second exposure. Also of note is that no mosquitoes even landed on the treated hands during these relatively lengthy exposures. Furthermore, the compositions were just as effective at repelling insects during a second exposure ninety minutes after application. While the density of mosquitoes in the Plexiglas box was, in all likelihood, greater than any to be encountered during normal situations, this alone does not guarantee that the invention will be effective in open areas. As a consequence, multiple trials were performed at various times of day in open areas, as described below.

Trial Example 3

The results of Trial Experiment 3 are summarized in Table 3. A test group of four people from various age groups were placed in an open area during the mid-afternoon without any treatment as a control and to check the biting nature of the mosquitoes. Within one minute, the test group incurred an average of three mosquito bites. Lemon juice was applied to the insect bites, which caused the pain and swelling to cease. To maintain the integrity of the experiment, lemon juice was used rather than the above-described compositions. However, the lemon juice does not lose any effectiveness at treating insect bites when part of the compositions of the Formula Examples. The composition according to Formula Example 1 was then applied to the exposed areas of all of the members of the test group, specifically the hands and face. No adverse reactions to the composition, such as burning or irritation of the skin, were reported by any of the members of the test group. Following application, the test group remained in the open area for a period of thirty minutes. During this time, no mosquito bites were incurred by any of the members of the test group. A fifteen minute interval passed before the test group returned to the open area for a second thirty minute interval. Even without further treatment, no mosquito bites were incurred during this period. Following another interval of thirty minutes, the test group returned to the open area for a third interval of thirty minutes. Despite the fact that nearly two hours and fifteen minutes had passed since application of the composition of Formula Example 1, no mosquito bites were incurred.

Trial Example 4

The results of Trial Example 4 are summarized in Table 4. A test group of three people from various age groups were placed in an open area during the early evening. Within one minute, the test group incurred an average of four mosquito bites. Lemon juice was applied to the insect bites, which caused the pain and swelling to cease. To maintain the integrity of the experiment, lemon juice was used rather than the above-described compositions. However, the lemon juice does not lose any effectiveness at treating insect bites when part of the compositions of the Formula Examples. The composition according to Formula Example 2 was then applied to the exposed areas of all of the members of the test group, specifically the hands and face. No adverse reactions to the composition, such as burning or irritation of the skin, were reported by any of the members of the test group. Following application, the test group remained in the open area for a period of thirty minutes. During this time, no mosquito bites were incurred by any members of the test group. A fifteen minute interval passed before the test group returned to the open area for a second thirty minute interval. Even without further treatment, no mosquito bites were incurred during this period. Following another interval of fifteen minutes, the test group returned to the open area for a third interval of thirty minutes. Despite the fact that nearly two hours had passed since application of the composition of Formula Example 2, no mosquito bites were incurred.

Trial Example 5

The results of Trial Example 5 are summarized in Table 5. A test group of three people from various age groups were placed in an open area during the morning. Within one minute, the test group incurred an average of three mosquito bites. Lemon juice was applied to the insect bites, which caused the pain and swelling to cease. To maintain the integrity of the experiment, lemon juice was used rather than the above-described compositions. However, the lemon juice does not lose any effectiveness at treating insect bites when part of the compositions of the Formula Examples. The composition according to Formula Example 3 was then applied to the exposed areas of all of the members of the test group, specifically the hands and face. No adverse reactions to the compositions, such as burning or irritation of the skin, were reported by any of the members of the test group. Following application, the test group remained in the open area for a period of thirty minutes. During this time, no mosquito bites were incurred by any members of the test group. A fifteen minute interval passed before the test group returned to the open area for a second thirty minute interval. Even without further treatment, no mosquito bites were incurred during this period. Following another interval of thirty minutes, the test group returned to the open area for a third interval of thirty minutes. Despite the fact that nearly two hours and fifteen minutes had passed since application of the composition of Formula Example 3, no mosquito bites were incurred.

The results of these experiments indicate that the compositions of all three Formula Examples constitute effective insect repellents in outdoor conditions irrespective of the time of day. Of note is that the compositions retain their repellent properties for at least two hours and fifteen minutes after application. More importantly, the compositions have not caused any adverse reactions in any of the subjects tested irrespective of age.

Since various modifications can be made in my invention as herein above described, and many apparently widely different embodiments of same made within the spirit and scope of the claims without departing from such spirit and scope, it is intended that all matter contained in the accompanying specification shall be interpreted as illustrative only and not in a limiting sense.

TABLE 1

RESULTS OF A STUDY ON THE EFFECTIVENESS OF AN INSECT REPELLENT PREPARED ACCORDING TO FORMULA EXAMPLE 3 AND LEMON JUICE AS A POSTBITE TREATMENT SOLUTION AT THE MOSQUITO LABORATORY IN WINNIPEG, MANITOBA, CANADA ON JUNE 26, 1996.

| TREATMENTS | TIME | NUMBNER OF BITES |
| --- | --- | --- |
| Control using untreated left hand of second person and placing it in the cage | 11.00 a.m. | 4 bites and 6 mosquitoes sat on hand in ten seconds |
| Sprayed and rubbed the areas around the mosquito bites of the left hand with Lemon juice | 11.01 a.m. | Pain and swelling stopped |
| Sprayed the right hand with insect repellent prepared according to Formula Example 3 with a mixture of Lemon oil and Cedarwood oil and placing the hand in the mosquito cage | 11.15 a.m. | No bite upto two minutes and no mosquito sat on the hand |
| The right hand previously sprayed at 11.15 a.m. with the insect repellent, with no further treatment and placing it again in the mosquito cage | 1.00 p.m. | No bites upto two minutes and no mosquito sat on the hand |

TABLE 2

RESULTS OF A STUDY ON THE EFFECTIVENESS OF INSECT REPELLENTS PREPARED ACCORDING TO FORMULA EXAMPLES 1 AND 2 AND LEMON JUICE AS A POSTBITE TREATMENT SOLUTION AT THE MOSQUITO LABORATORY IN WINNIPEG, MANITOBA, CANADA ON JUNE 26, 1996.

| TREATMENTS | TIME | NUMBER OF BITES |
| --- | --- | --- |
| Control using untreated left hand and placing it in the mosquito cage | 10.00 a.m. | 4 bites and 7 mosquitoes sat on hand in 10 seconds |
| Sprayed and rubbed the areas around the mosquito bites of the left hand with Lemon juice | 10.01 a.m. | Pain and swelling stopped |
| Sprayed the right hand with a insect repellent prepared according to Formula Example 1 with Lemon oil and placing the hand in the mosquito cage | 10.15 a.m. | No bite upto two minutes and no mosquito sat on the hand |
| Sprayed the left hand with the insect repellent prepared according to Formula Example 2 with Cedarwood oil and placing the hand in the mosquito cage | 10.30 a.m. | No bite upto two minutes and no mosquito sat on the hand |
| The right hand, previously sprayed with insect repellent prepared according to Formula Example 1 at 10.15 a.m. with no further treatment and placing the hand again in the mosquito cage | 11.45 a.m. | No bite upto two minutes and no mosquito sat on the hand |
| The left hand, previously sprayed with insect repellent prepared according to Formula Example 2 at 10.30 a.m. with no further treatment and placing the hand again in the mosquito cage | 12.00 Noon | No bite upto two minutes and no mosquito sat on the hand |

TABLE 3

RESULTS OF A STUDY ON THE EFFECTIVENESS OF AN INSECT REPELLENT PREPARED ACCORDING TO FORMULA EXAMPLE 1 AND LEMON JUICE AS A POSTBITE TREATMENT SOLUTION AT NEW DELHI, INDIA ON AUGUST 5, 1994.

| TREATMENT | NUMBER OF PEOPLE | TIME | AVERAGE NUMBER OF BITES |
|---|---|---|---|
| Control with no treatment on exposed hand and face. | 4 | 2.15 p.m. | 3 bites in one minute |
| Treated the bites with Lemon juice | 4 | 2.16 p.m. | Pain and swelling stopped |
| Sprayed the hands and face with the insect repellent prepared according to Formula Example 1 with Lemon oil, starting at 2.30 p.m. and staying outside in the open area for 30 minutes | 4 | 2.30 p.m. | No bites |
| No further treatment and sitting again in the same area starting at 3.15 p.m. for 30 minutes | 4 | 3.45 p.m. | No bites |
| No further treatment and sitting again in the same area starting at 4.15 p.m. for 30 minutes Experiment terminated | 4 | 4.45 p.m. | No bites |

TABLE 4

RESULTS OF A STUDY ON THE EFFECTIVENESS OF AN INSECT REPELLENT PREPARED ACCORDING TO FORMULA EXAMPLE 2 AND LEMON JUICE AS A POSTBITE TREATMENT SOLUTION AT PANIPAT, HARYANA, INDIA ON AUGUST 12, 1994.

| TREATMENT | NUMBER OF PEOPLE | TIME | AVERAGE NUMBER OF BITES |
|---|---|---|---|
| Control with no treatment on exposed hand and face. | 3 | 5.15 p.m. | 4 bites in one minute |
| Treated the bites with Lemon juice | 3 | 5.16 p.m. | Pain and swelling stopped |
| Sprayed the hands and face with the insect repellent prepared according to Formula Example 2 with Cedarwood oil, starting at 5.30 p.m. and staying outside in the open area for 30 minutes | 3 | 5.30 p.m. | No bites |
| No further treatment and sitting again in the same area starting at 6.15 p.m. for 30 minutes | 3 | 6.45 p.m. | No bites |
| No further treatment and sitting again in the same area starting at 7.00 p.m. for 30 minutes Experiment terminated | 3 | 7.30 p.m. | No bites |

TABLE 5

RESULTS OF A STUDY ON THE EFFECTIVENESS OF AN INSECT REPELLENT PREPARED ACCORDING TO FORMULA EXAMPLE 3 AND LEMON JUICE AS A POSTBITE TREATMENT SOLUTION AT HISSAR, HARYANA, INDIA ON AUGUST 19, 1994.

| TREATMENT | NUMBER OF PEOPLE | TIME | AVERAGE NUMBER OF BITES |
|---|---|---|---|
| Control with no treatment on exposed hand and face. | 3 | 8.15 a.m. | 3 bites in one minute |
| Treated the bites with Lemon juice | 3 | 8.16 a.m. | Pain and swelling stopped |
| Sprayed the hands and face with the insect repellent prepared according to Formula Example 3 with a mixture of Lemon oil and Cedarwood oil, starting at 8.30 a.m. and staying outside in the open area for 30 minutes | 3 | 8.30 a.m. | No bites |
| No further treatment and sitting again in the same area starting at 9.15 a.m. for 30 minutes | 3 | 9.45 a.m. | No bites |
| No further treatment and sitting again in the same area starting at 10.15 a.m. for 30 minutes Experiment terminated | 3 | 10.45 a.m. | No bites |

TABLE 6

RESULTS OF A STUDY ON THE EFFECTIVENESS OF AN INSECT REPELLENT PREPARED ACCORDING TO FORMULA EXAMPLE 1 AND LEMON JUICE AS A POSTBITE TREATMENT SOLUTION IN BACKYARD AND VEGETABLE GARDEN AREAS IN REGINA, SADKATCHEWAN, CANADA ON JULY 14, 1995.

| TREATMENT | NUMBER OF PEOPLE | TIME | AVERAGE NUMBER OF BITES |
|---|---|---|---|
| Control with no treatment on exposed hand and face. | 1 | 5.30 p.m. | 3 bites in one minute |
| Treated the mosquito bites with Lemon juice | 1 | 5.31 p.m. | Pain and swelling stopped |
| Sprayed the hands and face with the insect repellent prepared according to Formula Example 1 with Lemon oil, starting at 5.45 p.m. and staying outside in the backyard and garden area. | 1 | 5.45 p.m. | No bites |
| Continued staying in the backyard and garden area upto 6.45 p.m. with no further treatment | 1 | 6.45 p.m. | No bites |
| Coming back at 7.15 p.m. and staying in the backyard with no further treatment for 30 minutes. Experiment terminated | 1 | 7.45 p.m. | No bites |

TABLE 7

RESULTS OF A STUDY ON THE EFFECTIVENESS OF INSECT REPELLENTS PREPARED ACCORDING TO FORMULA EXAMPLES 1, 2 AND 3 AND LEMON JUICE AS A POSTBITE TREATMENT SOLUTION IN BUSH AREAS OF REGINA, SASKATCHEWAN, CANADA ON JUNE 16, 1996.

| TREATMENT | PERSON No. | TIME | NUMBER OF BITES |
|---|---|---|---|
| Control with no treatment on hand and face. | A | 2.00 p.m. | 4 bites in 1 minute |
| Treated the bites with Lemon juice | A | 2.01 p.m. | Pain and swelling stopped |
| Sprayed the hands and face with the insect repellent #1* and walked in the bush area | A | 2.15 p.m. | No bites |
| No further treatment and stayed outside in the bush area | A | 3.15 p.m. | No bites |
| No further treatment and stayed outside in the bush area | A | 4.20 p.m. | No bites |
| Control with no treatment on hand and face. | B | 2.30 p.m. | 3 bites in 1 minute |
| Treated the bites with Lemon juice | B | 2.31 p.m. | Pain and swelling stopped |
| Sprayed the hands and face with the insect repellent #2* and walked in the bush area | B | 2.40 p.m. | No bite |
| No further treatment and stayed outside in the bush area | B | 3.45 p.m. | No bite |
| No further treatment and stayed outside in the bush area | B | 4.50 p.m. | No bite |
| Control with no treatment on hand and face. | C | 2.45 p.m. | 4 bites in 1 minute |
| Treated the bites with Lemon juice | C | 2.46 p.m. | Pain and swelling stopped |
| Sprayed the hands and face with the insect repellent #3* and walked in the bush area | C | 2.50 p.m. | No bite |
| No further treatment and stayed outside in the bush area | C | 3.55 p.m. | No bite |
| No further treatment and stayed outside in the bush area | C | 5.00 p.m. | No bite |

*Insect repellents #1, 2 and 3 were prepared according to Formula Examples 1, 2 and 3 with Lemon oil, Cedarwood oil and a mixture of Lemon oil and Cedarwood oil respectively.

I claim:

1. A method of repelling insects comprising:
   providing a mixture consisting essentially of:
   5–60% active ingredient, selected from the group consisting of: lemon oil; cedarwood oil; and mixtures thereof;
   25–80% isopropyl alcohol;
   5–60% lemon juice or lime juice
   4–25% water; and
   less than 1% anti-oxidizing agent when the mixture does not contain lemon juice or lime juice; and
   repelling insects by applying the mixture to areas desired for protection.

2. A method of treating pain and swelling caused by an insect bite comprising:
   providing a solution consisting essentially of:
   15–75% active ingredient selected from the group consisting of: lemon juice; lime juice; and non-toxic organic acids;
   5–25% insect repelling agent selected from the group consisting of: lemon oil; cedarwood oil; and mixtures thereof;
   5–45% isopropyl alcohol; and
   5–25% water;
   locating the insect bite; and
   applying said solution topologically over the afflicted region, thereby reducing the pain, swelling and feelings to itch.

* * * * *